(12) United States Patent  
Ramirez Lobo

(10) Patent No.: US 8,012,190 B2  
(45) Date of Patent: Sep. 6, 2011

(54) DEVICE FOR THE TREATMENT OF CHEMICALLY DAMAGED HAIR AND ITS METHOD OF USE

(76) Inventor: Antonio Ramirez Lobo, Palm Bay, FL (US)

( * ) Notice: Subject to any disclaimer, the term of this patent is extended or adjusted under 35 U.S.C. 154(b) by 661 days.

(21) Appl. No.: 12/192,995

(22) Filed: Aug. 16, 2008

(65) Prior Publication Data

US 2010/0037479 A1 Feb. 18, 2010

(51) Int. Cl.
*A61N 5/01* (2006.01)
*A45D 20/00* (2006.01)

(52) U.S. Cl. .................. 607/90; 606/9; 607/88; 607/96; 128/898

(58) Field of Classification Search ... 606/9; 607/87–96
See application file for complete search history.

(56) References Cited

U.S. PATENT DOCUMENTS

| | | | |
|---|---|---|---|
| 4,263,500 A | 4/1981 | Springer | |
| 4,382,174 A | 5/1983 | Barns | |
| 6,053,180 A | 4/2000 | Kwan | |
| 7,258,695 B2 | 8/2007 | Carullo | |
| 2003/0023284 A1* | 1/2003 | Gartstein et al. | 607/88 |
| 2004/0064167 A1* | 4/2004 | Berry et al. | 607/89 |
| 2005/0090877 A1* | 4/2005 | Harth et al. | 607/88 |
| 2005/0256554 A1 | 11/2005 | Malak | |
| 2007/0032847 A1* | 2/2007 | Weckwerth et al. | 607/93 |

\* cited by examiner

*Primary Examiner* — Henry M Johnson, III
*Assistant Examiner* — Jeffrey Lipitz
(74) *Attorney, Agent, or Firm* — Ruben Alcoba, Esq.

(57) ABSTRACT

A device that treats chemically damaged hair by stimulating the circulation of blood and nutrients to the scalp while simultaneously promoting an environment that is not favorable for the propagation of bacteria. The device is composed of a blower that is attached to an air chiller. The blower houses a blue LED that irradiates a blue light outward from the mouth of blower. The device simultaneously blows cold air out of the mouth of the blower and irradiates the hair and scalp of the person being treated.

1 Claim, 2 Drawing Sheets

DEVICE FOR THE TREATMENT OF CHEMICALLY DAMAGED HAIR AND ITS METHOD OF USE

BACKGROUND

Figure 1:
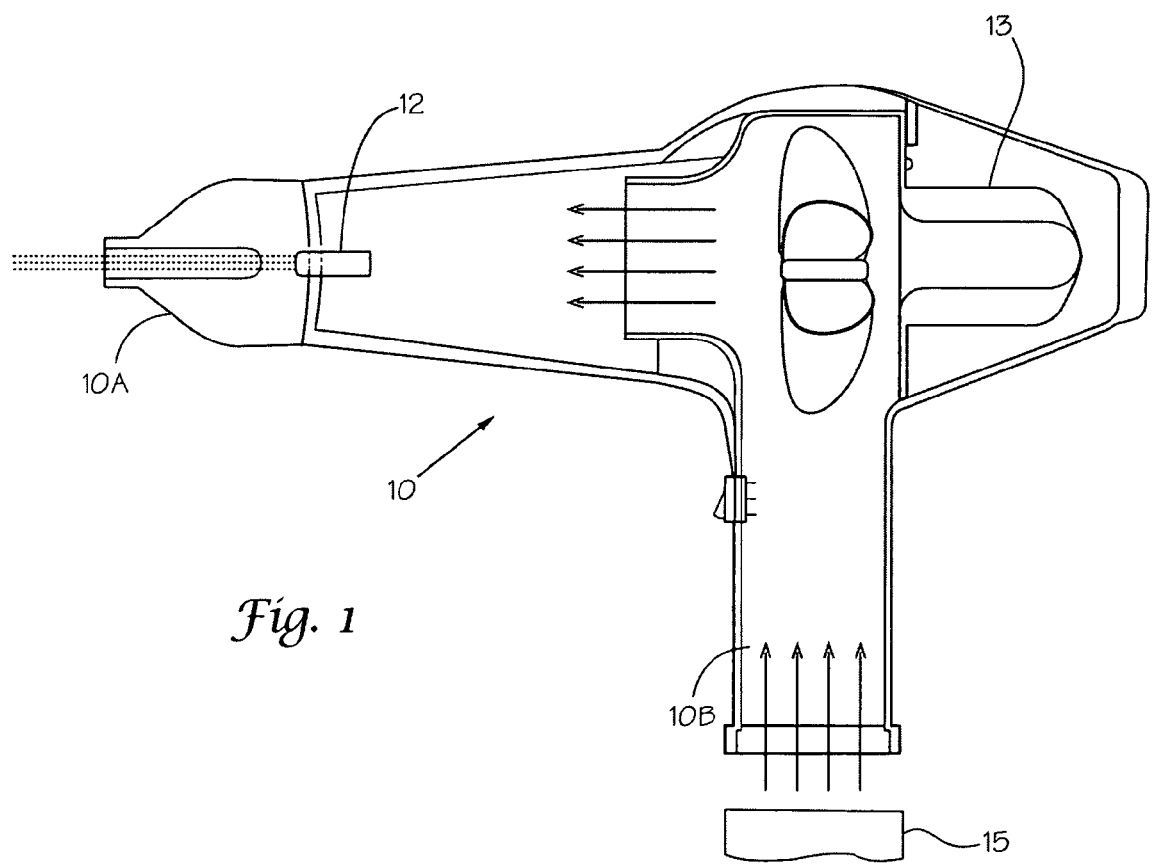

The present invention is directed to a device that treats chemically damaged hair.

The inventor of the present invention is a cosmetologist who has been treating hair for many years. During his career, he has seen many clients whose hair has been damaged by chemicals or over drying of the hair.

During the same period, he also has read many articles concerning the treatment of living tissues with light therapy. This caused the inventor to believe that he could treat his clients' chemically damaged hair and scalp using cold air and light therapy/radiation. He realized that he could not use a light that could further damage the scalp of the hair follicles of his clients.

From his experience, he knew that if he could stimulate the circulation of the scalp, that the hair follicles would receive more blood and nutrients, thereby speeding the process of healing damaged hair follicles. He also knew that hair that has been damaged by chemicals or because of excessive drying was not as strong as hair that had not been damaged, and that damaged hair is prone to being attacked by bacteria. Hair attacked by bacteria tends to have split ends, have an unhealthy look, and falls off prior to the hair cycle being completed.

He decided to invent a device that could treat chemically damaged hair by stimulating the circulation of blood and nutrients of the scalp while at the same time promoting an environment that would not be favorable for the propagation of bacteria. He decided to use a blue light-emitting diode (hereinafter referred as "LED") to irradiate the scalp, for he knew that the wavelength of the blue LED would not further damage the hair follicles, yet the blue LED would promote the production of free radicals that would destroy bacteria growing around the roots of the hair. He also knew that providing cold air to the scalp of a human promotes circulation.

The following U.S. Patents and Published Applications have addressed the treatment of hair using light therapy: Malak, U.S. Patent Application No. 2005/0256554 A1; Carullu et al., U.S. Pat. No. 7,258,695 B2; Springer et al., U.S. Pat. No. 4,263,500; Barns, U.S. Pat. No. 4,382,174; and Kwan, U.S. Pat. No. 6,053,180. None of the above inventions show a device that delivers cold air while at the same time irradiating an area with a blue LED for the treatment of chemically damaged hair. The cold air blown to the area must be in the range from about 40 degrees Fahrenheit to about 60 degrees Fahrenheit.

For the foregoing reasons, there is a need for a device that treats chemically damaged hair by stimulating the circulation of blood and nutrients to the scalp while simultaneously promoting an environment that is not favorable for the propagation of bacteria.

SUMMARY

The present invention is directed to a device for treating chemically damaged hair. The device works by stimulating the circulation of blood and nutrients to the scalp while simultaneously promoting an environment that is not favorable for the propagation of bacteria. The device for treating chemically damaged hair, comprises a chiller, a blower and an extension, the extension connects to the chiller and the blower The chiller can be selectively controlled to cool air from about 40 degrees Fahrenheit to about 60 degrees Fahrenheit.

The device is used by providing the device, turning the device on so that the blue light is on and that it blows cool air out, the air being at a temperature from about 40 degrees Fahrenheit to about 60 degrees Fahrenheit, and pointing the mouth of the blower over the scalp and the hair of a client who is being treated.

DRAWINGS

Figure 2:
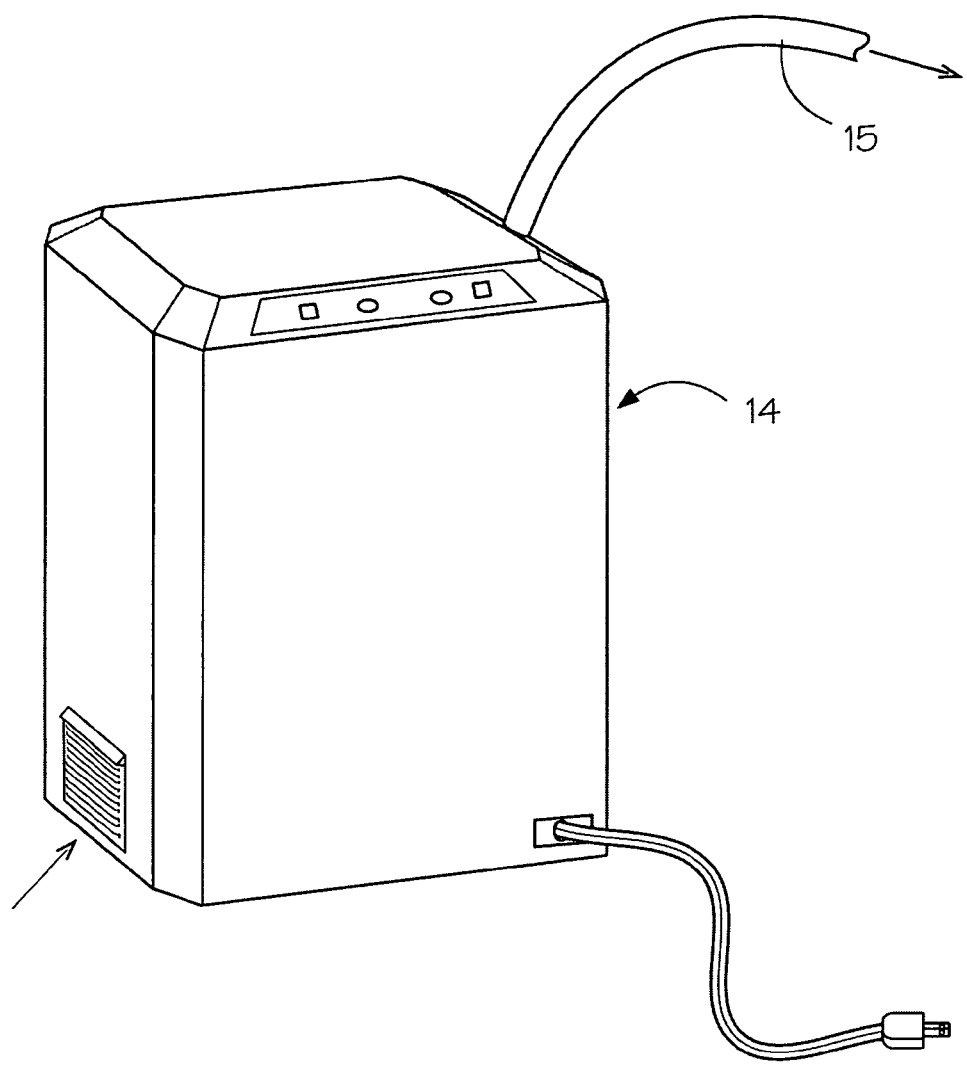

These and other features, aspects, and advantages of the present invention will become better understood with regard to the following description, appended claims, and drawings where:

FIG. 1 shows a cutaway view of the blower of the present invention and an extension that attaches to the blower; and FIG. 2 shows a perspective view of the chiller of the present invention.

DESCRIPTION

As seen in FIGS. 1-2, a device for treating chemically damaged hair comprising a chiller 14 that cools air and has the capacity to blow air outward, a blower 10, the blower 10 has a receiving end 10b and a mouth 10a, the blower 10 houses an LED 12 that emits a blue light outward, the LED 12 is attached to the blower 10 at a position that is adjacent to the mouth 10a and axially positioned, the blower 10 also has a fan 13 positioned between the mouth 10a and the receiving end 10b of the blower 10, the fan 13 blows air outward from the mouth of the blower 10a, and an extension 15 that plugs into the receiving end 10b of the blower 10 and to the chiller 14, the extension 15 allows fluid to pass from the chiller 14 to the blower 10.

In an embodiment of the present invention, the chiller 14 can be selectively controlled to cool air from about 40 degrees Fahrenheit to about 60 degrees Fahrenheit.

The present invention is used by turning the device on so that the blue LED 12 is on and that it blows cool air out, the air being at a temperature from about 40 degrees Fahrenheit to about 60 degrees Fahrenheit and pointing the mouth of the blower 10a over the scalp and the hair of a client who is being treated.

Although the present invention has been described in considerable detail with reference to certain preferred versions thereof, other versions are possible. Therefore the spirit and the scope of the claims should not be limited to the description of the preferred versions contained herein.

What is claimed is:

1. A method for treating chemically damaged hair comprising the steps of:
   providing a device that comprises:
      a chiller that cools air and has the capacity to blow air outward; a blower, the blower has a receiving end and a mouth, the blower has a fan positioned between the mouth and the receiving end of the blower, the fan flows air outward from the mouth of the blower, the blower houses an LED that emits a blue light outward, the LED is attached to the blower at a position that is adjacent to the mouth and axially positioned between the mouth and the fan of the blower; and an extension that plugs into tile receiving end of the blower and to the chiller, the extension allows fluid to pass from the chiller to the blower, turning the device on so that the blue light is on and that it blows cool air out, the air being at a temperature from about 40 degrees Fahrenheit to about 60 degrees Fahrenheit; and pointing the mouth of the blower over the scalp and the hair of a client who is being treated.

* * * * *